US00PP30306P3

(12) United States Plant Patent
Brulotte

(10) Patent No.: US PP30,306 P3
(45) Date of Patent: Mar. 26, 2019

(54) HOP PLANT NAMED 'BRU-1'

(50) Latin Name: *Humulus lupulus*
Varietal Denomination: BRU-1

(71) Applicant: Topp Hop Ranch, LLC, Toppenish, WA (US)

(72) Inventor: Reggie Brulotte, Toppenish, WA (US)

(73) Assignee: Topp Hop Ranch, LLC, Toppenish, WA (US)

( * ) Notice: Subject to any disclaimer, the term of this patent is extended or adjusted under 35 U.S.C. 154(b) by 0 days.

(21) Appl. No.: 15/732,209

(22) Filed: Oct. 2, 2017

(65) Prior Publication Data

US 2018/0098475 P1 Apr. 5, 2018

Related U.S. Application Data

(60) Provisional application No. 62/496,119, filed on Oct. 4, 2016.

(51) Int. Cl.
*A01H 5/00* (2018.01)
*A01H 5/02* (2018.01)

(52) U.S. Cl.
USPC ..... Plt./236
CPC ..... *A01H 5/02* (2013.01)

(58) Field of Classification Search
USPC ..... Plt./236
See application file for complete search history.

(56) References Cited

PUBLICATIONS http://www.yakimavalleyhops.com/Experimental_BRU_1_Hops_p/hopsexpbru1-1-2016crop.htm.*

* cited by examiner

*Primary Examiner* — Annette H Para
(74) *Attorney, Agent, or Firm* — Michelle Bos Legal LLC

(57) ABSTRACT

'BRU-1' is a new hop plant notable for its abundant, dense cones and distinct aroma.

7 Drawing Sheets

Latin name: *Humulus lupulus*.
Variety denomination: 'BRU-1'.

BACKGROUND OF THE VARIETY

'BRU-1' is a new and distinct variety of hop plant discovered by the inventor as a chance seedling in a cultivated 'Cascade' (not patented) hop field near Toppenish, Wash. 'BRU-1' variety has been asexually reproduced by cuttings near Toppenish, Wash. and has been observed to remain true to type over successive asexually propagated generations.

BRIEF DESCRIPTION OF THE VARIETY

'BRU-1' hop plant was first selected for its abundant, dense cones and distinct aroma. The cones of 'BRU-1' are similar in structure to 'Columbus' (U.S. Plant Pat. No. 10,956) and 'HBC 394' (U.S. Plant Pat. No. 21,289), but can be distinguished from 'Columbus' by their fruitier aroma, and from 'HBC 394' by their much higher alpha acid content. A comparison of 'BRU-1' to 'Columbus', 'HBC 394' and 'Cascade' appears in Table 1 below.

TABLE 1

Comparison of 'BRU-1' to Known Varieties

| | 'BRU-1' | 'Columbus' | 'HBC 394' | 'Cascade' |
|---|---|---|---|---|
| Cone shape | Rounded to conical | Rounded | Ovoid | Elongated |
| Cone compactness | Compact, dense | Compact | Compact | Loose |

TABLE 1-continued

Comparison of 'BRU-1' to Known Varieties

| | 'BRU-1' | 'Columbus' | 'HBC 394' | 'Cascade' |
|---|---|---|---|---|
| Aroma | Fruity, pineapple | Mild; light citrus | Citrus, tropical fruit | Fruity, citrusy, herbal |
| Alpha Acids | 13% to 15% | 14% to 16% | 11% to 13% | 4.5% to 7% |
| Yield (lbs/acre) | 2400 to 2600 | 2600-2700 | 1400 to 1600 | 1400 to 2000 |

BRIEF DESCRIPTION OF THE PHOTOGRAPHS

DETAILED BOTANICAL DESCRIPTION OF THE VARIETY

Figure 1:
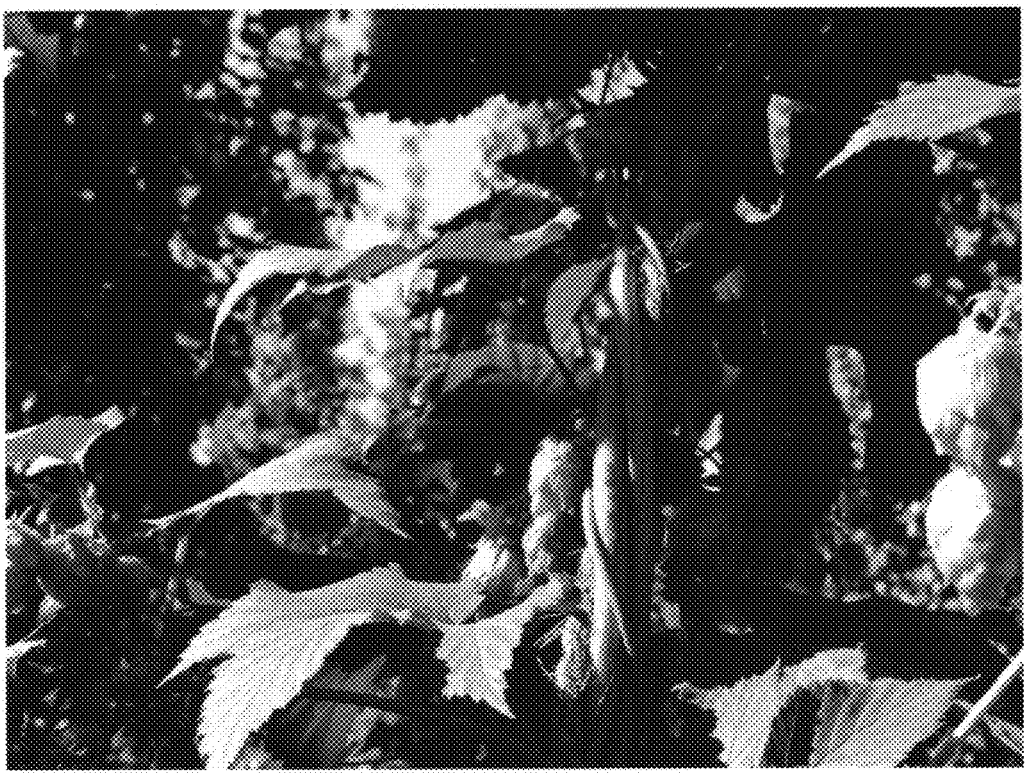
FIG. 1 shows the bine of the 'BRU-1' hop plant.
Figure 2:
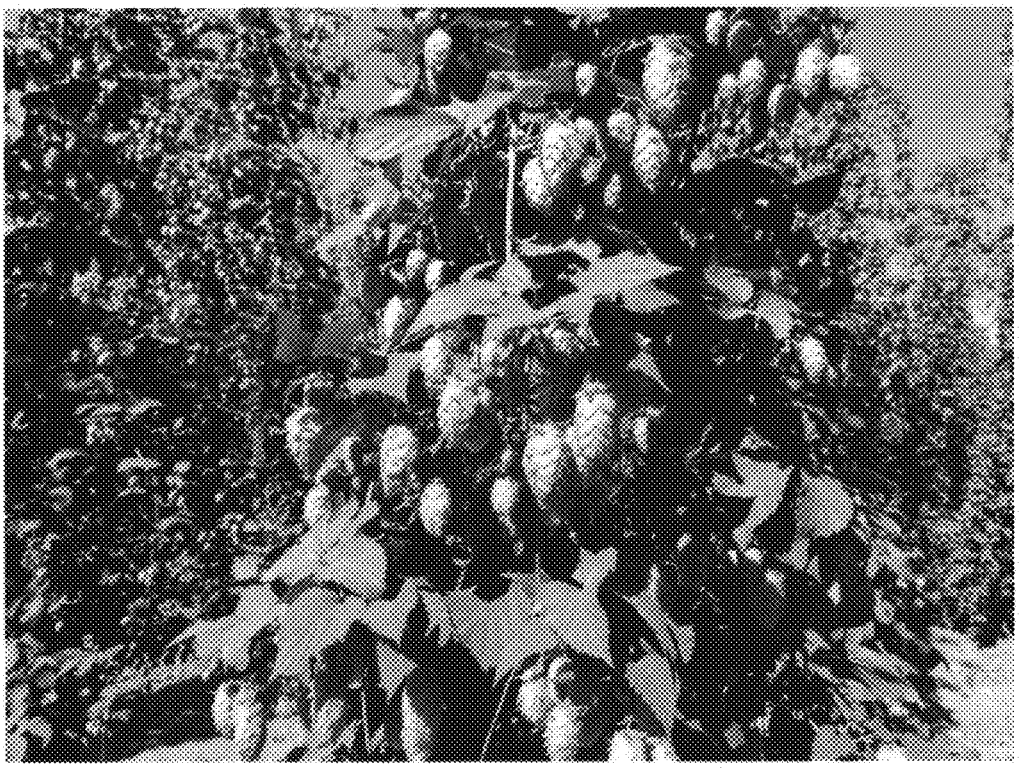
FIGS. 2 and 3 show cones and leaves of the 'BRU-1' hop plant.
Figure 3:
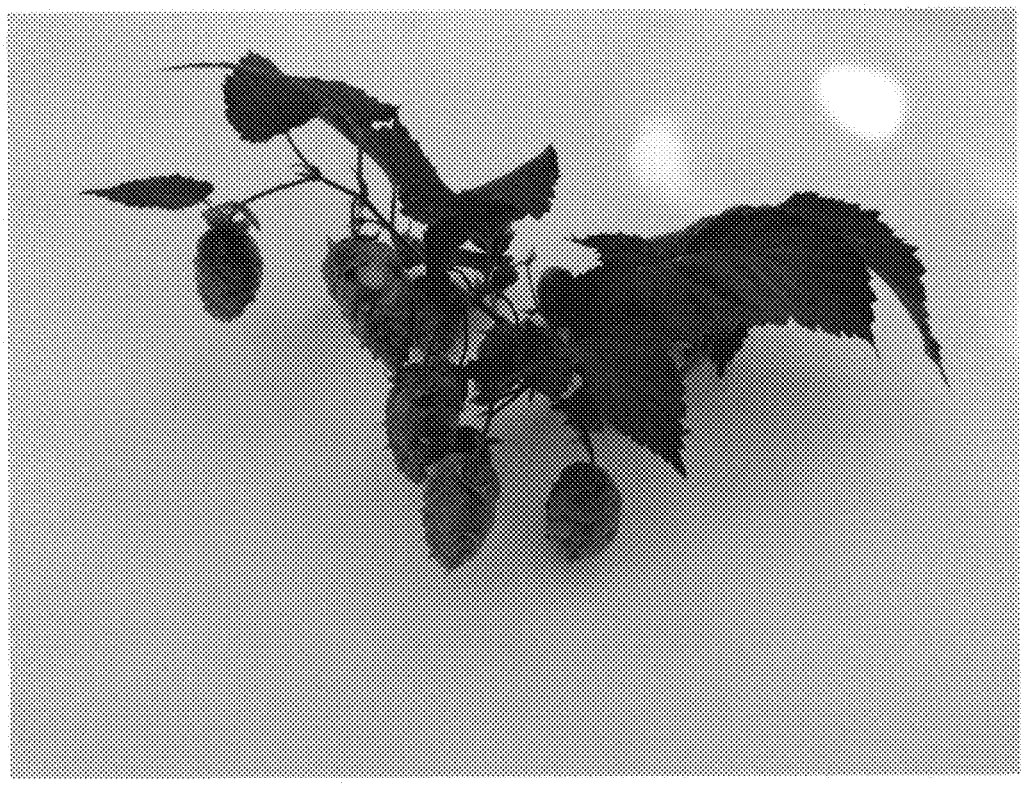
Figure 4:
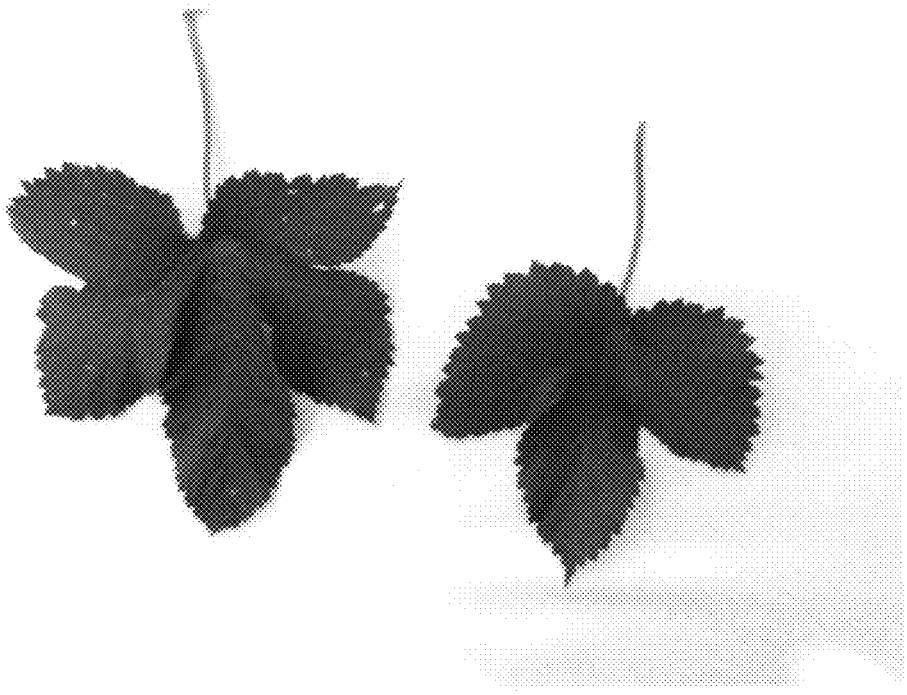
FIG. 4 shows the upper surface of a mature leaf of the 'BRU-1' hop plant.
Figure 5:
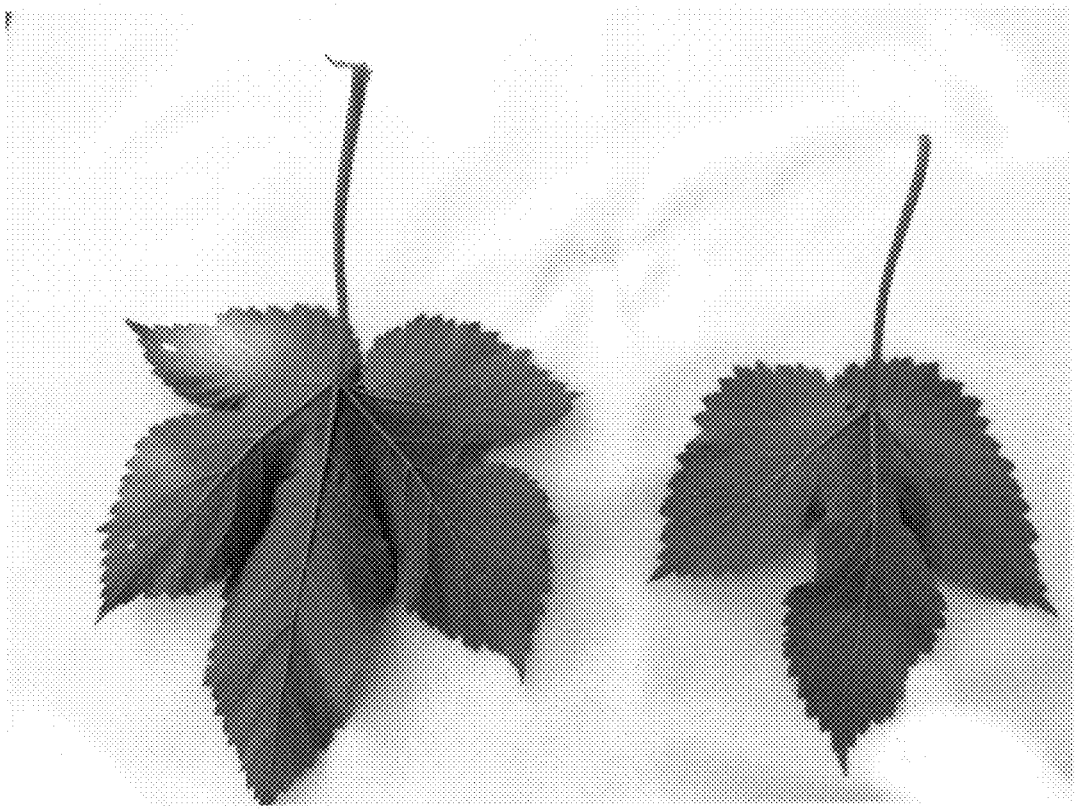
FIG. 5 shows the lower surface of a mature leaf of the 'BRU-1' hop plant.
Figure 6:
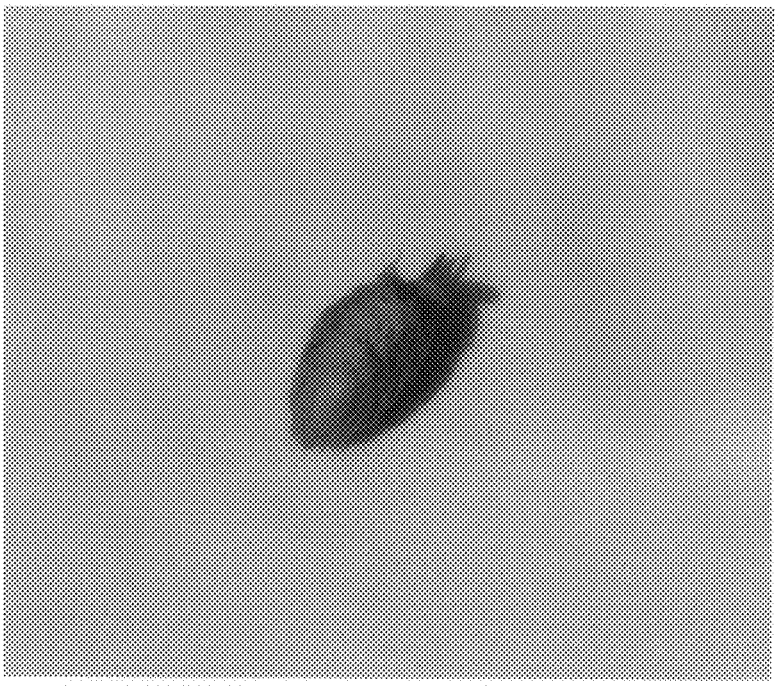
FIG. 6 shows a sectioned cone of the 'BRU-1' hop plant.
Figure 7:
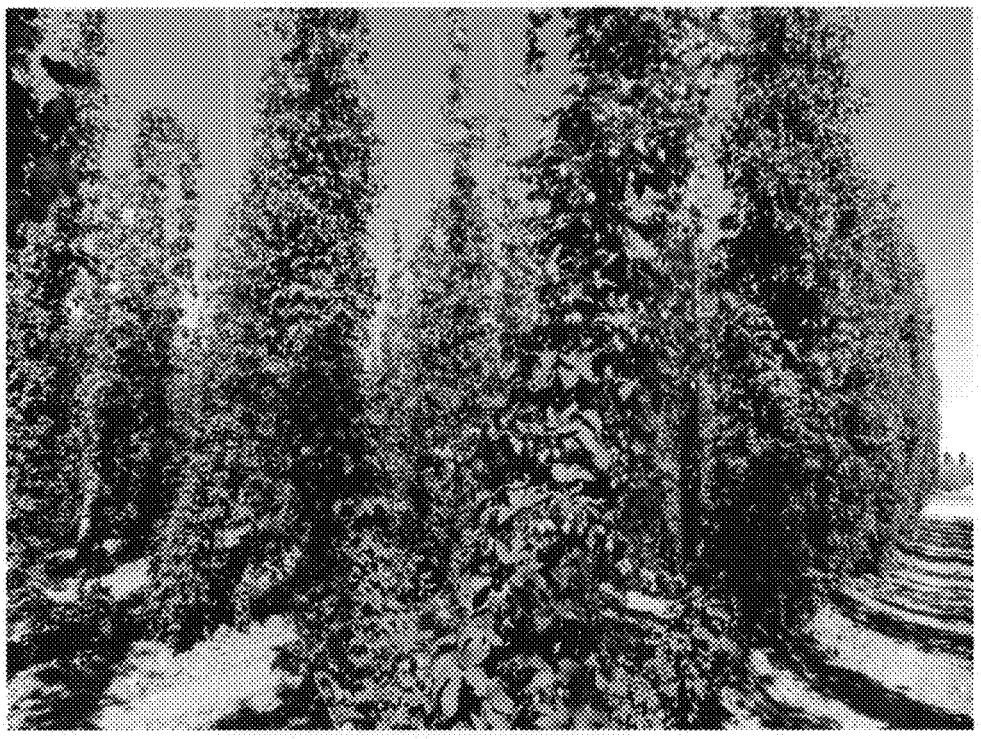
FIG. 7 shows a 'BRU-1' hop plant approximately 2 weeks before harvest.

The following-detailed botanical description is based on observations made during the 2016 growing season at Toppenish, Wash. of one-year-old plants. All colors are described according to The Royal Horticultural Society Colour Chart ($5^{th}$ ed. 2007). It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average.

Bine:

*Color*.—Yellow-green 145B.
*Stripe*.—Narrow, distinct.
*Stripe color*.—Greyed-purple 183B.
*Stipule color*.—Yellow-green 145A.
*Stipule direction*.—Outward.
*Average diameter*.—10 mm.
*Average internode distance*.—20 cm.
*Shoot emergence* (*timing*).—Late April, typical of aroma varieties.

Leaves:

*Leaf arrangement*.—Opposite.
*Leaf shape*.—Palmate.
*Average length* (*mature leaf*).—14 cm.
*Average width* (*mature leaf*).—18 cm.
*Color—upper surface, mature*.—Green N137B.
*Color—lower surface, mature*.—Greyed-green 191A.
*Color—upper surface, immature*.—Green N137A.
*Color—lower surface, immature*. —Greyed-green 191A.
*Number of leaf lobes*.—Mostly 3 or 5.
*Margin*.—Serrate and biserrate.
*Average serrations per inch*.—3 to 4.
*Leaf apex*.—Acuminate.
*Texture—upper surface*.—Glabrous.
*Texture—lower surface*.—Smooth, veins prominent.
*Pose*.—Horizontal to upward.
*Petiole length*.—6 cm to 10 cm.
*Petiole diameter*.—3 mm.
*Petiole color*.—Yellow-green 145B.
*Vein color*.—Yellow-green 145B.

Laterals:

*Length* (*at about* 40 *cm from ground*).—30 mm to 120 cm.
*Diameter*.—3 mm to 4 mm.
*Color*.—Yellow-green 145B.
*Internode length*.—12 cm to 20 cm.
*Stipule position*.—Upward.
*Stipule color*.—Yellow-green 145A.

Cones:

*Average length*.—30 mm to 40 mm, usually about 30 mm.
*Average diameter*.—12 mm to 25 mm, usually about 18 mm.
*Average number of cones per basal lateral node*.—8 to 14, usually about 10.
*Bract color* (*outer surface*).—Yellow-green 145A.
*Bract color* (*inner surface*).—Yellow-green 145A.
*Cone shape*.—Rounded to conical with pointed tip.
*Cone compactness*.—Compact, dense.
*Average cone weight*.—0.625 g.
*Bract shape*.—Ovate.
*Bract tip shape*.—Acuminate.
*Bract tip position*.—Recurved.
*Bract length*.—12 mm.
*Bract width*.—12 mm.
*Bracteole shape*.—Obovate.
*Bracteole tip shape*.—Cuspidate.
*Bracteole length*.—13 mm.
*Bracteole width/diameter*.—12 mm.
*Bracteole color*.—Yellow-green 145B.
*Strig size, compactness*.—Bulky, tightly held, large as compared to cone size.
*Lupulin glands*.—Moderate amount, yellow 3A.
*Yield per acre*.—2400 lbs. to 2600 lbs.
*Harvest maturity*.—Mid- to mid-late season, September 15 to 20.
*Shattering potential at harvest*.—Very low.
*Disease resistance/susceptibility*.—Mild susceptibility to powdery mildew (*Podosphaera macularis*); some susceptibility to downy mildew (*Pseudoperonospora humuli*) in spring.
*Aroma*.—Fruity, pineapple.

Analytical data:

*Alpha acids* (*spectrophotometric method*).—13% to 15%.
*Beta acids*.—8% to 10%.
*Total oil*.—1.5 to 2.0 ml/100 g.
*Myrcene* (*as % of total oils*).—50% to 55%.
*Caryophyllene* (*as % of total oils*).—7% to 8%.
*Humulene* (*as % of total oils*).—9% to 11%.
*Farnesene* (*as % of total oils*).—<1%.

I claim:

1. A new and distinct hop plant (*Humulus lupulus*) substantially as described and illustrated herein.

* * * * *